US010408746B2

(12) United States Patent
Spartz et al.

(10) Patent No.: US 10,408,746 B2
(45) Date of Patent: Sep. 10, 2019

(54) SYSTEM AND METHOD FOR IMPURITY DETECTION IN BEVERAGE GRADE GASES

(71) Applicant: MLS ACQ, Inc., East Windsor, CT (US)

(72) Inventors: Martin L. Spartz, Ellington, CT (US); Peter Paul Behnke, Vernon, CT (US); Charles Mark Phillips, Sicklerville, NJ (US); Adam R. Klempner, Gardner, MA (US); Anthony S. Bonanno, Ellington, CT (US)

(73) Assignee: MLS ACQ, Inc., East Windsor, CT (US)

(*) Notice: Subject to any disclaimer, the term of this patent is extended or adjusted under 35 U.S.C. 154(b) by 0 days.

(21) Appl. No.: 15/910,621

(22) Filed: Mar. 2, 2018

(65) Prior Publication Data
US 2018/0252639 A1 Sep. 6, 2018

Related U.S. Application Data

(60) Provisional application No. 62/466,697, filed on Mar. 3, 2017, provisional application No. 62/468,573, filed on Mar. 8, 2017.

(51) Int. Cl.
G01N 21/3504 (2014.01)
G01N 21/64 (2006.01)
(Continued)

(52) U.S. Cl.
CPC ....... G01N 21/3504 (2013.01); G01N 21/643 (2013.01); G01N 21/75 (2013.01);
(Continued)

(58) Field of Classification Search
CPC .... G01N 21/3504; G01N 33/00; G01N 21/64; G01N 21/94; G01N 21/03; G01N 21/05; G01N 21/75; G01N 21/17; G01N 21/35; G01N 21/84; G01N 21/643; G01N 21/031; G01N 2021/8411; G01N 2021/354;
(Continued)

(56) References Cited

U.S. PATENT DOCUMENTS 6,748,334 B1 * 6/2004 Perez ................. G01N 21/3504
702/24
9,606,088 B2 3/2017 Spartz et al.
(Continued)

FOREIGN PATENT DOCUMENTS

EP 1 840 557 3/2007
GB 769997 3/1957

OTHER PUBLICATIONS

"Monitor Trace Impurities in Carbon Dioxide Used in Carbonated Beverages and Food Packaging," (2013).
(Continued)

Primary Examiner — David P Porta
Assistant Examiner — Meenakshi S Sahu
(74) Attorney, Agent, or Firm — HoustonHogle LLP

(57) ABSTRACT

A system and method for determining impurities in a beverage grade gas such as $CO_2$ or $N_2$ relies on a coupling of FTIR analysis and UV fluorescence detection. Conversion of reduced sulphur present in some impurities to $SO_2$ can be conducted using a furnace. In some cases, $CO_2$ % also is determined.

20 Claims, 4 Drawing Sheets

(51) Int. Cl.
  *G01N 21/75* (2006.01)
  *G01N 21/94* (2006.01)
  *G01N 33/00* (2006.01)
  *G01N 21/35* (2014.01)
  *G01N 21/03* (2006.01)
  *G01N 21/05* (2006.01)
  *G01N 21/17* (2006.01)
  *G01N 21/84* (2006.01)

(52) U.S. Cl.
  CPC .......... *G01N 21/94* (2013.01); *G01N 21/031* (2013.01); *G01N 21/0317* (2013.01); *G01N 21/05* (2013.01); *G01N 33/0013* (2013.01); *G01N 33/0042* (2013.01); *G01N 2021/174* (2013.01); *G01N 2021/1734* (2013.01); *G01N 2021/354* (2013.01); *G01N 2021/3595* (2013.01); *G01N 2021/8411* (2013.01)

(58) Field of Classification Search
  CPC ..... G01N 2021/174; G01N 2021/1734; G01N 21/0317; G01N 33/0013; G01N 2021/3595; G01N 33/0042

USPC .................................................. 250/339.08
  See application file for complete search history.

(56) References Cited

U.S. PATENT DOCUMENTS

2005/0079625 A1    4/2005   Akashi et al.
2015/0260695 A1    9/2015   Spartz et al.
2016/0231239 A1    8/2016   Kotidis et al.

OTHER PUBLICATIONS

Flavio da Silveira Petruci, J., et al., "Online Analysis of H2S and SO2 via Advanced Mid-Infrared Gas Sensors," Anal. Chem., 87: 9605-9611 (2015).
International Search Report and Written Opinion of the International Searching Authority, dated May 8, 2018, from International Application No. PCT/US2018/020672, filed on Mar. 2, 2018 24 pages.
"BevAlertTM Analytical System," Mocon Baseline (2018).

* cited by examiner

SYSTEM AND METHOD FOR IMPURITY DETECTION IN BEVERAGE GRADE GASES

RELATED APPLICATIONS

This application claims the benefit under 35 USC 119(e) of U.S. Provisional Application No. 62/466,697, filed on Mar. 3, 2017, and U.S. Provisional Application No. 62/468,573, filed on Mar. 8, 2017, both being incorporated herein by reference in their entirety.

BACKGROUND OF THE INVENTION

Carbon dioxide ($CO_2$) is a colorless, odorless gas that can be used as an inert material, as pressurized gas, in "dry ice", liquid or supercritical fluid applications, and many other areas, such as, for instance, oil production and the chemical industry. In the food sector, $CO_2$ is a medium for decaffeination and a feedstock for obtaining carbonated beverages, providing effervescence to water, soft drinks, wine, beer and so forth. Applications such as found in the beverage industry require $CO_2$ of a specified purity. It is important, therefore, to monitor the nature and levels of contaminants in the gas employed.

Some existing systems for analyzing impurities in $CO_2$ gas rely on gas chromatography (GC), with photoionization detection (PID) and/or flame ionization detection (FID). GC systems, however, can be slow, requiring several (e.g., 6-8) minutes between samples.

Other approaches rely on mass spectrometry (MS), a technique that is fast but can suffer from cross interferences and calibration issues. As with other MS systems, continued maintenance is often required.

Specialized instrumentation geared toward detecting a particular contaminant (total sulfur, for instance) or a class of contaminants (e.g., aromatics) also have been developed. This approach, however, provides limited information. A sensor designed to focus on aromatic compounds, for instance, may fail to signal the presence of acetaldehyde or nitrogen oxides ($NO_x$). One or more additional devices might be needed to analyze for other contaminants. Combining multiple instruments, however, can result in cumbersome calibrations and extensive maintenance.

SUMMARY OF THE INVENTION

A need continues to exist, therefore, for systems and techniques that can address problems associated with the approaches described above. For gases used in the beverage industry, $CO_2$ or $N_2$, for example, there is a need for systems and methods that can detect and measure a wide variety of impurities (at parts per million (ppm) or even parts per billion (ppb) levels). In the case of $CO_2$, a need also exists for determining the quality of the gas being employed.

Generally, the invention combines Fourier transform infrared (FTIR) gas analysis and UV fluorescence for measuring impurities in beverage grade gases.

Some of its aspects feature a system that comprises a FTIR component and a sulfur analyzer. The latter includes an oxidizing furnace for converting reduced sulfur present in a gas sample to $SO_2$ and a UV fluorescence analyzer for measuring $SO_2$. The system can be fully integrated and, in specific implementations, can provide measurements of $CO_2$ %, thereby assessing the quality of the $CO_2$ used.

Other aspects of the invention feature a method for measuring impurities in beverage grade gas such as $CO_2$, for example. In the method, a sample is split between an FTIR analyzer and an apparatus designed to determine sulfur levels. The latter includes a furnace for converting reduced sulfur to $SO_2$. An ultraviolet (UV) fluorescence analyzer can be used to measure $SO_2$ levels.

Further aspects of the invention feature a system for measuring impurities in a beverage grade gas. The system includes a FTIR analyzer, an oxidizing furnace for converting reduced sulfur present in a sample to $SO_2$, and a manifold for directing the $SO_2$ from the oxidizing furnace to the FTIR analyzer.

Embodiments of the invention present many advantages. In the beverage industry, for example, the tolerance for many impurities is very low, in the range of parts per million (ppm) or even parts per billion (ppb), for example. The system and method described herein can offer a fast and sensitive assessment of trace amounts while providing simultaneous readings of multiple contaminants. Both organic (e.g., volatile organic compounds or VOCs) as well as inorganic impurities such as total sulfur, sulfur oxides ($SO_x$, e.g., $SO_2$) can be detected. Amounts of all the aromatics and aliphatics can be correctly summed up. Methane can be measured individually. Approaches described herein can detect and measure moisture, a critical contaminant that can be introduced during truck delivery. Levels of $SO_2$, total sulfur and total reduced sulfur also can be determined.

While the existing approaches described above are not designed to give information regarding the quality of the $CO_2$ gas, a quality that can be affected by the presence of nitrogen gas ($N_2$) or air, the system and method described herein can measure and report $CO_2$ percentages in the gas being sampled.

The system offers faster measurement time, less calibration, analysis of more compounds, the capacity to measure multiple species and, in some cases, lower MDLs. In many instances the system offers a fully integrated impurity measurement system with a response times that can be down to 5 seconds. Typically, the approaches described herein do not require calibrations for the FTIR data.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
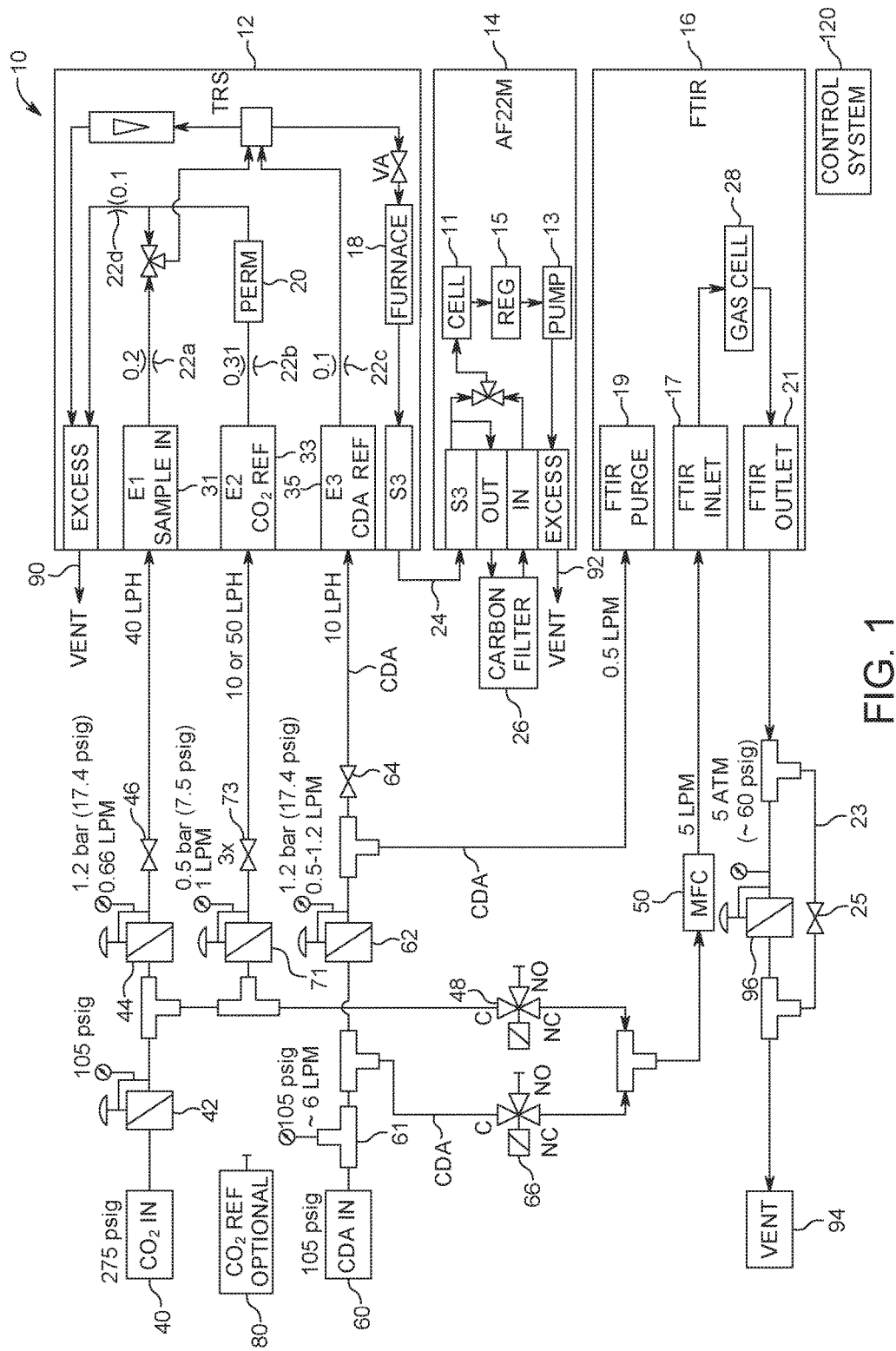
FIG. 1 is a diagram of a system that can be used to detect impurities in beverage grade gases.

The above and other features of the invention including various details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

In many of its aspects, the invention relates to detecting impurities in beverage grade gases, for instance impurities present in carbon dioxide ($CO_2$) gas and/or nitrogen gas ($N_2$). In some cases, total $CO_2$ amounts in a sample gas are determined as well.

$CO_2$ purity often depends on the $CO_2$ manufacturing process, plant purification methods, storage, transportation, point of use conditions and so forth. For the food and beverage sectors, for example, $CO_2$ is obtained via combustion, fermentation, from ammonia and hydrogen production. Both the preparation and the supply chain, often complex, that ultimately deliver the $CO_2$ to users can introduce impurities in the $CO_2$. Some of the contaminants particularly important to bottlers include acetaldehyde, benzene, methanol, total sulfur content and total hydrocarbons. Guidelines regarding $CO_2$ quality and best practices have been formulated by the International Society of Beverage Technologists® (ISBT), a group including beverage and $CO_2$ producers, distributors, providers of analytical and other related services and equipment.

The system and method described herein rely on a coupling of a Fourier transform infrared (FTIR) gas analysis and UV fluorescence for measuring impurities in beverage grade $CO_2$ and $N_2$, for example, or in other applications that place purity requirements on a gas. Examples of impurities that can be detected and quantified include but are not limited to: $SO_2$, total sulfur, $NH_3$, CO, NO, $NO_2$, $H_2O$, HCN, $CS_2$, hydrogen cyanide, methanol, moisture, acetaldehyde, methane, total hydrocarbons (methane, ethane, propane, pentane), benzene and total aromatic hydrocarbons and others. In some implementations, the $CO_2$ % present in the sample gas also is determined.

The FTIR spectrometer 16 can be, for instance, a Multi-Gas 2030 FTIR gas analyzer with a 1 millimeter (mm) 7 micrometer (μm) TE-cooled detector mercury cadmium telluride (HgCdTe or MCT) detector, with a pressure transducer rated to 6,000 Torr. While other detectors can be employed, the TE-cooled MCT detector does not require liquid nitrogen (LN2) and can offer a better signal to noise ratio (SNR) than a standard 0.25 mm detector. In comparison to the more conventional technology based on deuterated triglycine sulfate (DTGS), MCT detectors are not as affected by vibrations, since data collection is in the high kHz to MHz range. Specific examples employ a 9 micron (μm) cutoff detector that had a low frequency cutoff around 1,000 $cm^{-1}$. In other examples, use of a 7 μm TE-cooled MCT can provide an improvement in SNR by 3 to 5 times, resulting in 3 to 5 times lower minimum detection limits (MDLs), an important feature for benzene which has the lowest MDL requirement of 20 ppbv. MDL or Method Detection Limit is defined by the Environmental Protection Agency (EPA) as the minimum concentration of a substance that can be measured and reported with 99% confidence that the analyte concentration is greater than zero; it is determined from analysis of a sample in a given matrix containing the analyte.

The cell 28 used by the FTIR spectrometer, also referred to as the "gas cell" or "sample cell" can be made from a suitable material, for instance welded stainless steel. In many embodiments, it is fabricated to withstand pressures higher than atmospheric. In specific examples, the cell 28 is designed for pressures such as 2, 3, 4, 5 or higher atmospheres (atm) and 35° C. The cell 28 can be a flow through gas cell designed for flow rates such as, for instance, 2 to 5 liters per minute or 2000 to 3000 sccm (standard cubic centimeter per minute). Often, the source pressure is considerably higher than the pressure in the gas cell and a pressure regulator is included.

Increasing the pressure in gas cell 28 can improve sensitivity. Using high pressures of $CO_2$ is feasible since $CO_2$ does not absorb strongly in the spectral region in which impurities typically absorb. Thus, high amounts of $CO_2$ in the cell are not expected to interfere with the spectral features observed for the contaminants. Another gas that can be monitored for impurities is $N_2$. With no absorption in the region of interest, even higher (above 5 atm, for example) pressures of $N_2$ can be introduced in the cell, limited only by the materials and construction of the cell.

Typically, the gas cell windows are $BaF_2$ or $CaF_2$ and for many applications they too are designed to handle pressures higher than atmospheric, such as the pressures discussed above. Windows that are not water sensitive and do not have high refractive indices are preferred.

Some embodiments utilize a multiple reflection gas cell, such as, for instance, a White cell. Traditional White cells arrangements include three spherical concave mirrors having the same radius of curvature. Modified White cells or other multiple path designs, e.g., Herriott cells, Pfund cells, cavity-ring down cells, and integrating spheres, also can be employed, as described by Spartz et al. in U.S. Patent Application Publication No. 2015/0260695 A1, with the title *Process and System for Rapid Sample Analysis*, published on Sep. 17, 2015, now U.S. Pat. No. 9,606,088, both documents being incorporated herein by this reference in their entirety. By increasing the path length traveled, multiple-pass arrangements can measure low concentration components or detect weak absorption spectral features without increasing the physical length or volume of the cell itself.

Larger path lengths can be used in combination with higher reflective coatings such as enhanced silver.

In one non-limiting example, the gas cell 28 uses non-spherical concave mirrors to improve image quality and optical throughput. The mirrors are cut onto a single metal or a glass blank, providing a fixed path length; the mirrors can be the solid end caps of the gas cell, allowing for smaller sample cells that are easier to align. For a White type cell with a volume of about 200 mL, using gold mirrors can produce a path length of about 5.11 meters (m), while enhanced silver mirrors can result in a path lengths of 10 m or longer.

In further examples, the sample cell is a light pipe flow through sample cell.

In many cases, the FTIR 16 is run at 4 $cm^{-1}$ resolution at about 5 second data collection with Triangle or other Apodization. A rolling average of 1 to 5 minutes can be used with display updates at 5 to 6 second intervals. A lower resolution, such as 8 cm$^{-1}$ resolution, might provide somewhat better MDLs for some of the compounds of interest like benzene and the total aromatics. Using too low a resolution may result in losses in the capability of measuring some of the narrow absorbing gases.

Configurations can be designed to obtain 1 ppb MDL for benzene. All other compounds can be detected with improvements of 100 to 1000 over the values required by the ISBT.

In practice, benzene often can be used as a surrogate for all aromatic impurities. Since all the aromatic impurities absorb in the same spectral region (3000-3200 cm$^{-1}$) and can be measured as a group by measuring just one, it is possible to quantify for benzene and report as benzene and total aromatic hydrocarbon content. Preferably, linear regression is used to determine the area under the spectral plot in this aromatic region. In general, these aromatic compounds produced about the same signal per MOL.

Light VOCs such as methane, ethane, propane and pentane can be measured for the aliphatic hydrocarbons (most are in the 2750-3000 cm$^{-1}$ region).

In many instances, an FTIR with a multiple pass White cell has a large dynamic range over 0 to 500 ppm; accuracy/linearity/drift of +/-1%; $CO_2$ measurement of 100%+/-0.1%; MDL for impurities of 1-3 ppb; and MDL for total sulfur of 1 ppb.

Another implementation utilizes technology that combines the separation power of chromatography with the quantification power of absorption spectroscopy, as described, for example by U.S. Pat. No. 9,606,088. This approach can be particularly useful in detecting VOCs, for example.

In many cases the FTIR spectrometer 16 is provided with calibrations for a large number of impurities. Others can be added.

One approach described herein only measures impurities in a $CO_2$ sample. Another measures not just contaminants but also the amount of $CO_2$ present in the $CO_2$ sample gas, ($CO_2$ %). The latter determination is performed by having a high purity $CO_2$ source, for obtaining a reference measurement, or a high purity $CO_2$ calibration spectrum resident on the computer, e.g., in a calibration database, which can be compared with the collected spectra. The results can show whether the gas is low quality, containing, for example, significant amounts of $N_2$ or $O_2$.

In addition to measuring $CO_2$ %, the calibration also serves to remove the $CO_2$ spectral features while quantifying the impurities. This spectrum must match closely or errors will occur in the analysis for the impurities.

In some examples, a source of ultrahigh purity $CO_2$ 80 be added in order to supply the system with a high purity reference gas.

Turning to contaminants that contain sulfur, an oxidizing furnace (operating at a suitable temperature, e.g., 980° C.) is employed to convert all the reduced sulfur to $SO_2$. Total sulfur is measured by UV fluorescence and includes any $SO_2$ initially present in the sample along with the $SO_2$ generated by the oxidizing furnace from reduced sulfur compounds (e.g., $H_2S$, $CH_3SH$, $CS_2$, COS (carbonyl sulfide), $(CH_3)_2S$, $(CH_3)_2S_2$, and so forth).

The FTIR spectrometer 16 can measure $SO_2$ directly, so the amount of reduced sulfur can be calculated by comparing the FTIR reading with that obtained from the sulfur UV fluorescence analyzer 14.

In practice, the $CO_2$ is mixed with CDA (Clean Dry Air) to oxidize all the sulfur compounds. In some embodiments, one or both streams (i.e., CDA and/or the $CO_2$ gas sample) is/are preheated, to a suitable temperature, prior to entering the furnace 18, to facilitate the oxidation reaction. Suitable means for heating the gases include heat exchangers, heating tape, heating jackets, ovens, Peltier heaters, cartridge heaters, and so forth. It is also possible to preheat a stream obtained by combining (mixing) CDA and $CO_2$. In many cases, the gas stream(s) will be at a temperature within a range of from room temperature, to a temperature that is equal to or lower than the temperature of the furnace.

The UV fluorescence analyzer 14 may need to be calibrated occasionally, so a permeation tube with COS is present in the analyzer to calibrate the instrument. An example of existing technology designed to measure total reduced sulfur compounds and sulfur dioxide ($SO_2$) is the Environment S.A. AF22M-TRS Analyzer, available from Altech Environment U.S.A. This instrument is capable of monitoring sulfur compounds, such as, for example, $H_2S$, $CH_3SH$, $CS_2$, COS, $(CH_3)_2S$, $(CH_3)_2S_2$, and can work in three selectable modes: cyclic $SO_2$/TRS, continuous $SO_2$ and continuous TRS. In specific examples, a permeation tube 20 is provided as part of the TRS analyzer.

In another approach, the oxidation furnace 18 is used to generate the $SO_2$, essentially as described above, but in this embodiment the resulting $SO_2$ is directed to the FTIR analyzer 16 rather than to the UV fluorescence instrument. The UV fluorescence analyzer 14 can thus be bypassed or even eliminated from the overall system, the latter option resulting in reducing costs and a streamlined design. Calibration requirements would be reduced or eliminated (due to the FTIR detection). On the other hand, eliminating the UV fluorescence analyzer 14 may increase measurement times, as one gas would need to be measured, then the other. Effecting changes in pressure between the FTIR and the sulfur determination may lead to sensitivity losses and add complexity.

The system has one and preferably more than one sample inputs, to handle, for example, truck delivery, bulk and purified bulk samples. Automatic switching between the various channels can be provided. In many cases, input process gas streams from different points of the carbonation process or plant (e.g., delivery tanker, pre- or post-filtration and so forth), along with zero gas and validation gas are controlled. If desired, the system and method described herein can be integrated with the plant design.

FIG. 1 is a diagram of one illustrative implementation of a system that includes a FTIR analyzer 16, a furnace 18 utilized for TRS determinations and a UV fluorescence analyzer 14. Also included are conduits and equipment for directing gases and for controlling pressures and flows used in operating the system 10.

More specifically, shown in FIG. 1 is system 10 including: TRS converter 12, UV fluorescence analyzer 14, and FTIR spectrometer 16.

TRS converter 12 includes furnace 18, where, in the presence of heat and an oxidizing gas such as oxygen, sulfur-containing compounds yield $SO_2$. Typically, the $SO_2$ output from the furnace and, more generally from the TRS converter unit, will include (i) $SO_2$ present as such in the sample gas, and (ii) $SO_2$ generated through the conversion taking place in the furnace.

TRS converter 12 can be provided with permeation device 20 and several restrictors, e.g., 22a, 22b, 22c and 22d. Inputs 31, 33 and 35 can be used for introducing, respectively, the $CO_2$ sample, a $CO_2$ reference gas (ultra-pure $CO_2$, for example) and CDA. Other elements may be present, as known in the art. In some cases, TRS converter 12 is a commercial apparatus or a unit thereof.

$SO_2$-containing output from furnace 18 and more generally from TRS converter 12 (stream 24, for example) can be directed to UV fluorescence analyzer 14 (capable of measuring $SO_2$ levels and thus determining a total $SO_2$ amount (including initial $SO_2$ present in the sample as $SO_2$ and $SO_2$ obtained by converting sulfur-containing impurities in furnace 18). In some cases, UV fluorescence analyzer 14 also can be used to measure $SO_2$ levels directly, e.g., $SO_2$ levels present in a gas sample, a calibration or reference gas or a purge gas. Using the two determinations, amounts of impurities containing reduced sulfur can be obtained by subtracting the measurement of initial $SO_2$ present as such in the sample gas from the measurement of $SO_2$ in the output obtained from furnace 18.

The fluorescence analyzer 14 includes cell 11, pump 13 and regulator 15. Filter 26, containing activated charcoal, for instance, can be used to trap gas contaminants such as, for example, aromatic hydrocarbons. Other components can be included, as known in the art. In many cases, UV analyzer 14 is a commercial unit or part of a commercial unit. In one example, the UV analyzer is a Model AF22M UV analyzer.

In some embodiments, UV fluorescence analyzer 14 is bypassed or eliminated and the output from furnace 18 (and more generally from TRS converter 12) is directed to FTIR analyzer 16 using, for example, a manifold including suitable conduits, valves, flow controls, pressure regulators and/or other devices.

FTIR spectrometer 16 (e.g., a MultiGas 2030 FTIR apparatus) includes sample cell 28. As described above, sample cell 28 can be configured as a multiple path cell, a White or modified White cell, for example. In specific embodiments, the cell is configured to withstand pressures higher than atmospheric.

System 10 further includes various arrangements for supplying and directed gases to one or more of the units (modules) described above, namely to the TRS converter, the UV fluorescence analyzer and/or FTIR analyzer. Source 40, for instance, provides the $CO_2$ gas sample being evaluated. The pressure of the sample gas can be reduced, e.g., from 275 psig (pounds per square inch gauge) to 105 psig, using pressure regulator 42. In general, for best performance, the pressure of the gas inside the instrument 10 is in the range of _____.

The sample is split, conduits, valves, regulators, flow controls and other devices being provided for directing part of the sample $CO_2$ to TRS converter 12 and another part to FTIR analyzer 16. In the arrangement shown in FIG. 1, a first $CO_2$ portion enters the TRS converter 12 at a flow rate of 40 liters per hour (LPH) after passing through pressure regulator 44 and valve 46. A second $CO_2$ portion is conducted through a suitable valve 48, a ⅔ port solenoid valve for water, air and vacuum, for example, and mass flow controller (MFC) 50 to enter FTIR analyzer 16 at a flow rate of 5 liters per minute (LPM) through FTIR inlet 17.

If desired, a portion of the $CO_2$ sample being analyzed can be fed to the UV fluorescence analyzer for a direct measurement of initial $SO_2$ levels present in the sample.

Clean dry air (CDA) is brought in from source 60, via pressure regulator 62 and valve 64 to provide $O_2$ for TRS converter 12. In one example, its pressure is reduced from 105 psig to 17.4 psig; an initial flow rate of about 6 LPM is decreased first to about 0.5 to 1.2 LPM, entering TRS converter 12 (input 35) at a flow rate of 10 LPH.

CDA also can be used in FTIR analyzer 16. For example, a portion of the CDA stream exiting pressure regulator 62 is used to purge the FTIR optics, entering the FTIR analyzer at a flow rate of, e.g., 0.5 LPM, through FTIR purge inlet 19. Another portion of CDA can be split before the CDA stream enters pressure regulator 62 and can be directed to flow control 50 and FTIR analyzer 16 via valve 66, e.g., a ⅔ port solenoid valve for water, air and vacuum, or another suitable device. Valve 61 can be used to adjust the pressure of the CDA obtained from CDA source 60.

In conjunction with a CDA purifier (e.g., a suitable purifier model obtained from Parker Hannifin Corp.), not shown in FIG. 1, purified CDA can be used as zero and purge for the FTIR. Other implementations employ $N_2$ for zeroing and for purging the FTIR.

In some examples, system 10 is configured to supply a reference CO gas, e.g., from source 80, a gas tank, for example, that can be used in the analysis of the $CO_2$ sample from source 40. In one example, the reference $CO_2$ gas is an ultra-high purity $CO_2$ gas. In another example, the reference $CO_2$ gas is used for calibration purposes, e.g., to introduce a known amount of COS to the TRS converter (e.g., via pressure regulator 71 and valve 73). Further implementations utilize a purification device (carbon filter or another suitable trap) capable of removing contaminants present in the $CO_2$ sample gas and generate purified $CO_2$ gas. The latter can be used as the reference $CO_2$, in the FTIR analyzer, for example.

System 10 includes various vents (see, e.g., vents 90, 92 and 94) for the release of gases from the various units (modules) discussed above. Vent 94 is used in conjunction with pressure regulator 96 to address the above atmospheric pressure (e.g., several atmospheres) of the gas exiting gas cell 28 through FTIR outlet 21. Bypass conduit 23 is provided with valve 25.

The system can include control system 120, typically a computer system for collecting, analyzing and reporting the data. Other features that can be provided include touch screen technology, PLC and MFC control of gas streams, multiple (e.g., 4) automated sample channels, pressure controls for $CO_2$, $N_2$ and/or CDA inputs. Ethernet, Modbus and/or other can be used for data communication and remote control.

In one example, operation of a system such as system 10 is conducted as follows.

Before a sample is collected both analyzers are zeroed either by CDA or $N_2$ This can take place once a day, more frequently or at other suitable intervals.

The $CO_2$ sample is introduced into the system from one of several (i.e., two or more) locations from a facility or plant that uses $CO_2$. In one example, the $CO_2$ sample is provided from one of up to four (4) locations at the plant. The system automatically selects the gas to be analyzed or the selection can be made manually by the user. The chosen sample is split between the FTIR analyzer and the sulfur analyzer, in many embodiments the TRS converter 12. The pressure to the FTIR is maintained at 5 atm, while the sample to the converter 12 is dropped to a few pounds per square inch gauge (psig).

The FTIR sample is constantly being measured by the FTIR every 5 to 6 seconds and reported. The data are normally averaged from 1 to 5 minutes to lower the MDLs and remove process fluctuations. The FTIR reports $CO_2$ % and all the impurities except total sulfur.

Reference $CO_2$ that is ultra-pure can be utilized to obtain a baseline FTIR spectrum. This reference $CO_2$ 80 can be a separate cylinder of known-pure gas or can be the sample $CO_2$ that has been passed through carbon filters.

In specific examples, the reference $CO_2$ in the FTIR sample cell is maintained at a pressure higher than atmospheric, e.g., a pressure that is the same or similar to the pressure of the sample $CO_2$ in the gas cell. IR features of the reference $CO_2$ can be subtracted from the IR features of the sample $CO_2$, resulting in spectral features that can be used to identify impurities.

If reference $CO_2$ 80 has water, the spectral signatures of these interference can be subtracted from the reference spectra for the pure $CO_2$. Care must be taken, however, to avoid negative concentrations. Specifically, the reference spectrum is reviewed for any positive biases.

Alternatively or additionally, calibrations for high purity $CO_2$ can be resident on the computer system or accessible to it. For instance, $CO_2$ calibration spectra can be available in a database.

The sulfur analyzer, e.g., using the UV fluorescence analyzer described above, generates a constant reported concentration that is also averaged over time. These data can be used to calculate total reduced sulfur by subtracting the $SO_2$ initially present in the sample gas as $SO_2$, as measured by the FTIR.

Figure 2:
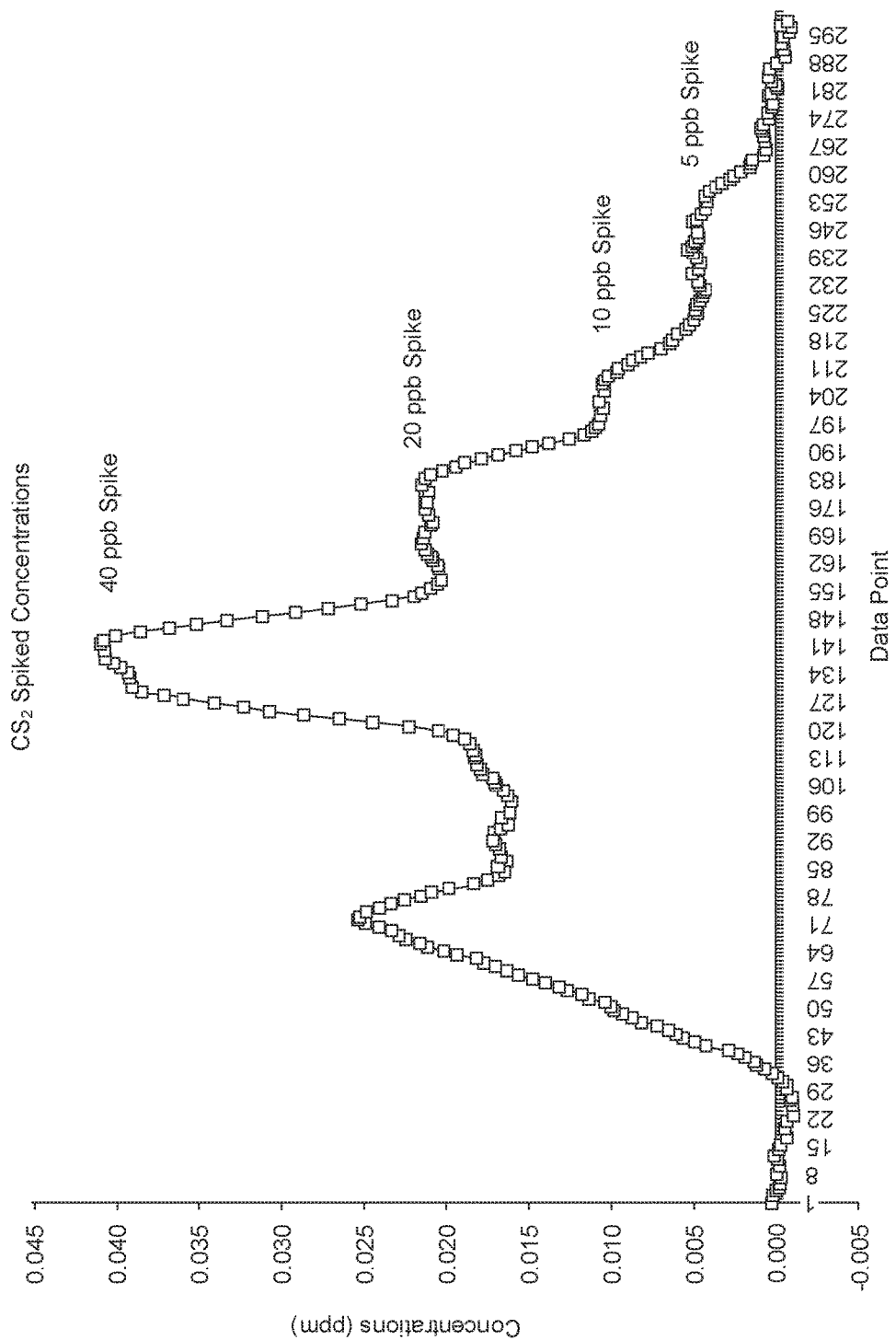
FIG. 2 is a plot of $CS_2$ spiked concentrations obtained using embodiments of the invention.
Figure 3:
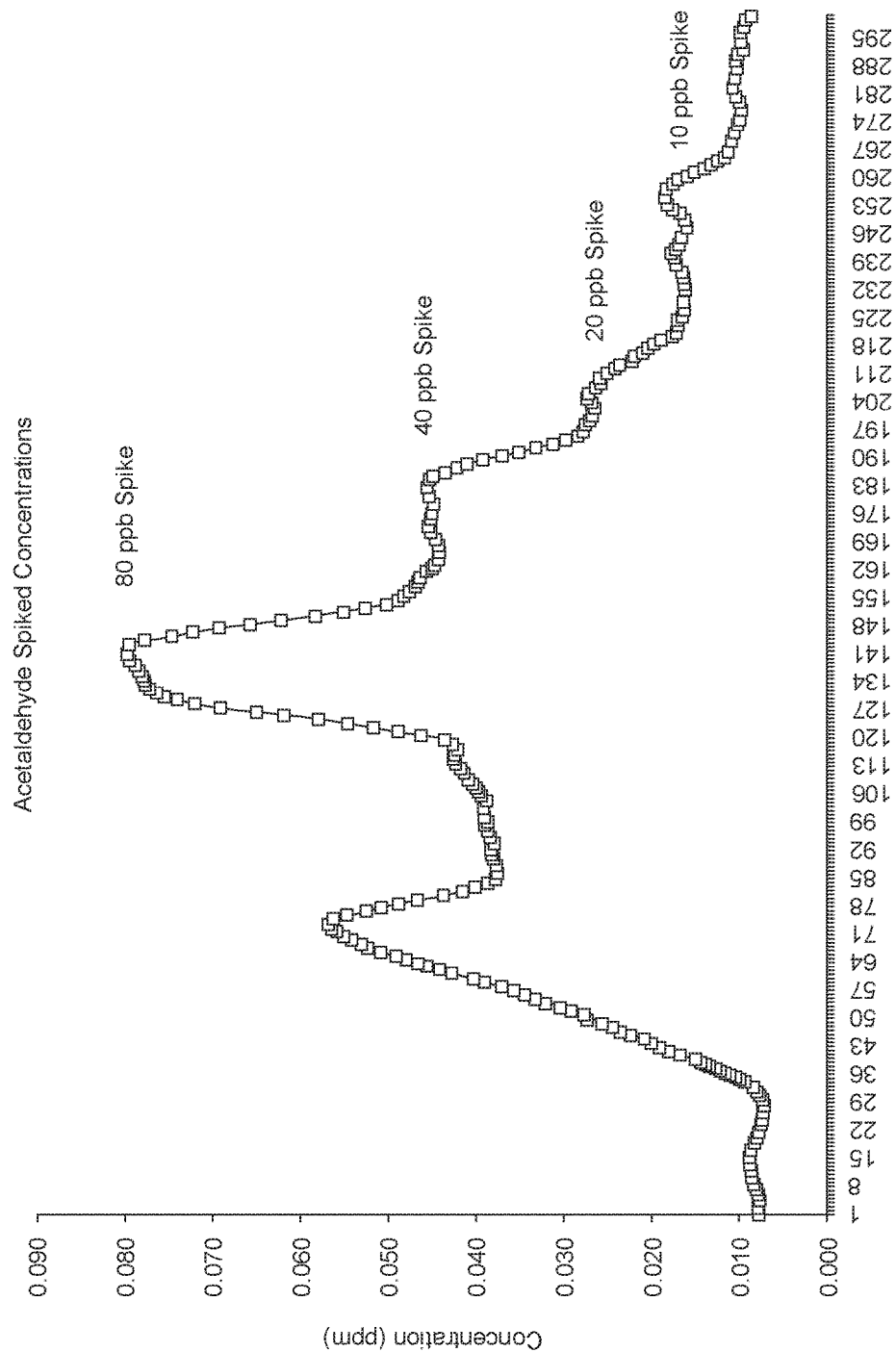
FIG. 3 is a plot of acetaldehyde spiked concentrations obtained using embodiments of the invention.
Figure 4:
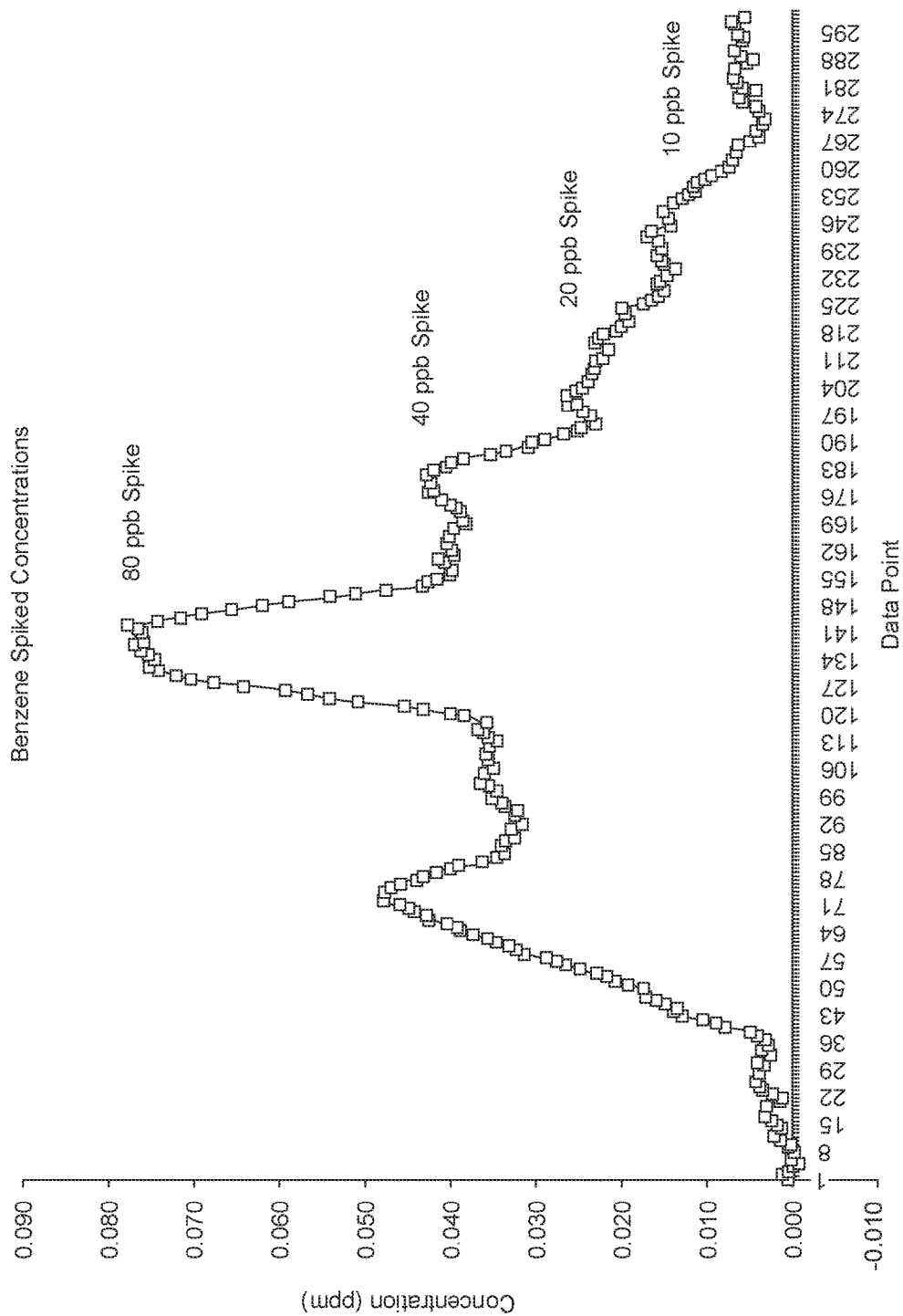
FIG. 4 is a plot of benzene spiked concentrations obtained using embodiments of the invention.

FIGS. 2-4 are plots of typical impurities that were spiked into the process $CO_2$ to demonstrate the technique and technology as described herein.

Further details are provided in the non-limiting example below.

EXAMPLE

In this example (referencing FIG. 1), the FTIR is provided with three sample options: (1) off: (2) zero: and (3) sample. The FTIR is controlled by a multi gas software suite such as, for example, the MG2000, reporting to a suitable display software via an AK Interface, for instance. Two solenoid valves (elements 48 and 66 in FIG. 1) and a mass flow controller (MFC 50 in FIG. 1) control sample stream selection and flow rates. When the instrument is in the "off" sample selection, both valves are closed and no gas reaches the FTIR 16. In the zero sample selection, the CDA or nitrogen valve 66 is opened and the MFC 50 is set to a suitable flow rate such as, for example, 5,000 standard cubic centimeter per minute (sccm). After purging the system (e.g., for 10-15 minutes) a new background can be taken in the MG2000 software. This background allows a clean reference single beam for comparison to new sample data.

The instrument is then placed in sample mode, the nitrogen valve 66 is closed and the $CO_2$ valve 48 is opened. The MFC remains set at 5,000 sccm, however due to the composition of $CO_2$, a conversion factor of 0.7 is applied to the total flow. Therefore the resultant flow is actually 3,800 sccm. In the sample mode, the current single beam is compared to the reference single beam and an absorbance spectrum is created. Absorbance spectra are analyzed via classical least squares (CLS) fitting to determine the level of contaminants present in the $CO_2$ stream. Both the background and the sample are analyzed at 5 atm to eliminate difference due to pressure. The measurement at 5 atm is important as it allows a significant decrease in detection limits by pressuring the analysis (gas) cell. This can be controlled by a manual back pressure regulator that is set prior to the collection of the background or sample gases. Calibrations for all contaminant gases were collected at the analysis conditions as well prior to deployment. Parameters associated with this configuration of the FTIR are summarized in Table 1:

TABLE 1

| (FTIR) | | | |
|---|---|---|---|
| Step | Gas | Flow (sccm) | Pressure (ATM) |
| Zero | Nitrogen ($N_2$) | 5,000 | 5 |
| Sample | Carbon Dioxide ($CO_2$) | 3,800 | 5 |

The TRS (total reduced sulfur) analyzer 12 used in this example also has three options: (1) Zero; (2) Span; and (3) Sample, and is controlled by its own independent software. The correct flow rates can be set via regulators internal to the particular system. Once thermally stable, the TRS analyzer 12 is placed into zero mode, where the sample $CO_2$ is scrubbed via a charcoal filter to remove contaminants and then analyzed. The instrument zero value is taken via the internal reference zero function. Next, the instrument is placed into Span mode where the reference $CO_2$ is drawn across a permeation bench 20 to introduce a known level of COS into the system. This then is converted to $SO_2$ via the furnace 18 and measured by the instrument. The internal auto span function corrects the calibration curve to the span response. After these two calibration steps are conducted, the instrument is placed into sample mode where any sulfur species is converted to $SO_2$ and then reported via the instrument. The calibration and measurement steps are performed at ambient pressure (1 atm). Any sample stream switching is controlled by an integrated box, not the sulfur analyzer itself.

Table 2 shows a possible configuration for the TRS analyzer:

TABLE 2

| (TRS Analyzer) | | | |
|---|---|---|---|
| Step | Gas | Flow (sccm) | Pressure (ATM) |
| Zero | Carbon Dioxide ($CO_2$), scrubbed | 667 | 1 |
| Span | Carbon Dioxide ($CO_2$), Permeation Bench | 667 | 1 |
| Sample | Carbon Dioxide ($CO_2$) | 667 | 1 |

The display is via a software program that can, for example, pull current data from the MG2000 software via a suitable interface such as, for example, an AK interface and data from the TRS analyzer via a Modbus or another suitable protocol. It allows users to identify maximum allowable concentrations for all gases, warning percentages for a list of gases, and the amount of time to average data. Additionally, it can include controls for sample switching for the FTIR. After pulling in and averaging the data, the concentrations of contaminants are displayed, and a graphical representation of the data can be shown via a bar chart on the right. Both the concentration and its corresponding bar can change between green, yellow, and red, for instance, based upon the user settings for maximum concentrations and warning percentages.

In some cases, the software handles a single inlet sample. Other designs can sample between several (e.g., four or more) inlet streams. In further implementations, functionality is added to create an instrument validation stream internal to the instrument that can allow users to measure a known concentration of gases via the FTIR to ensure the instrument is working properly.

While this invention has been particularly shown and described with references to preferred embodiments thereof, it will be understood by those skilled in the art that various changes in form and details may be made therein without departing from the scope of the invention encompassed by the appended claims.

What is claimed is:

1. A system for measuring impurities in a beverage grade gas, the system comprising:
 a high purity $CO_2$ source;
 a FTIR component including a gas cell configured for pressures higher than atmospheric and receiving the beverage grade gas for testing and $CO_2$ from the high purity $CO_2$ for providing a reference measurement; and
 a sulfur analyzer including an oxidizing furnace for converting reduced sulfur present in a sample to $SO_2$ and a UV fluorescence apparatus for determining total $SO_2$ amounts in the sample.

2. The system of claim 1, wherein the FTIR component includes a gas cell that is a multiple path type cell.

3. The system of claim 1, further comprising a computer for collecting, analyzing and/or reporting data.

4. The system of claim 1, further comprising software for collecting, analyzing and/or reporting data.

5. The system of claim 1, further comprising calibration information for pure $CO_2$ and/or one or more impurity.

6. The system of claim 1, wherein the FTIR component is provided with a mercury cadmium telluride detector.

7. A method for analyzing a beverage grade gas, the method comprising:
 directing a first portion of a gas sample to a FTIR gas cell;
 measuring impurities present in the gas cell under pressure with reference to $CO_2$ from the high purity $CO_2$ source;
 directing a second portion of the gas sample to an oxidizing furnace;
 converting reduced sulfur present in the second portion to $SO_2$; and
 measuring a total $SO_2$ in the second portion of the gas sample.

8. The method of claim 7, wherein the total $SO_2$ is the sum of $SO_2$ initially present in the second portion of the gas sample and $SO_2$ converted from reduced sulfur.

9. The method of claim 7, wherein total $SO_2$ measured in the second portion of the gas is compared with $SO_2$ measured by FTIR in the first portion of the gas sample to determine a TRS amount.

10. The method of claim 7, wherein data obtained for impurities in the first portion of the gas sample are compared with calibration data.

11. The method of claim 7, wherein a $CO_2$ % in the first portion of the gas sample is determined by FTIR and compared to calibration information.

12. The method of claim 7, wherein the first portion of the gas sample in the gas cell is at a pressure higher than atmospheric pressure.

13. The method of claim 7, wherein the impurities are selected from the group consisting of $SO_2$, total sulfur, $NH_3$, CO, NO, $NO_2$, $H_2O$, HCN, $CS_2$, hydrogen cyanide hydrogen cyanide, methanol, moisture, acetaldehyde, methane, total hydrocarbons, benzene and total aromatic hydrocarbons.

14. The method of claim 7, wherein the gas sample is obtained from a location in a plant.

15. The method of claim 7, wherein the beverage grade gas is $CO_2$ or $N_2$.

16. The method of claim 7, wherein total $SO_2$ is measured by UV fluorescence or by FTIR spectrometry.

17. A system for measuring impurities in a beverage grade gas, the system comprising:
 a FTIR analyzer including a gas cell configured for pressures higher than atmospheric and receiving the beverage grade gas for testing and $CO_2$ from a high purity $CO_2$ for providing a reference measurement;
 an oxidizing furnace for converting reduced sulfur present in a sample to $SO_2$; and
 a manifold for directing the $SO_2$ from the oxidizing furnace to the FTIR analyzer.

18. The system of claim 17, wherein the FTIR analyzer includes a gas cell.

19. The system of claim 17, wherein the gas cell is a multiple pass type cell.

20. The system of claim 17, wherein the gas cell is a flow through gas cell.

* * * * *